United States Patent [19]

Alexander et al.

[11] Patent Number: 4,537,772

[45] Date of Patent: Aug. 27, 1985

[54] ENHANCING ABSORPTION OF DRUGS FROM GASTROINTESTINAL TRACT USING ACYLCARNITINES

[75] Inventors: Jose Alexander; Joseph A. Fix, both of Lawrence, Kans.

[73] Assignee: Merck & Co., Inc., Rahway, N.J.

[21] Appl. No.: 606,054

[22] Filed: May 2, 1984

[51] Int. Cl.³ .................. A61K 31/52; A61K 31/54; A61K 31/70; A61K 31/195; A61K 31/205; A61K 31/505; A61K 37/00

[52] U.S. Cl. ............................................ 514/9; 514/3; 514/263; 514/261; 514/42; 514/192; 514/556; 514/561; 514/906; 514/869

[58] Field of Search ............... 424/316, 177, 180, 246, 424/251, 253, 519

Primary Examiner—Stanley J. Friedman
Attorney, Agent, or Firm—Manfred Polk; Michael C. Sudol, Jr.; Mario A. Monaco

[57] ABSTRACT

Acylcarnitines used as drug absorption enhancing agents for orally and rectally administered drugs.

16 Claims, No Drawings

ENHANCING ABSORPTION OF DRUGS FROM GASTROINTESTINAL TRACT USING ACYLCARNITINES

BACKGROUND OF THE INVENTION

The invention relates to a novel method and compositions for enhancing absorption of drugs from the gastrointestinal tract by incorporating therein an acylcarnitine absorption enhancing agent.

DESCRIPTION OF THE PRIOR ART

Although numerous references describe carnitine-acylcarnitine translocase system in mitochondria, the instant use of acylcarnitines to promote gastrointestinal drug absorption constitutes a novel and unobvious use of said acylcarnitine compounds. The carnitine-acylcarnitine translocase system has been localized in skeletal muscle, cardiac muscle, epididymal tissue, liver, kidney and brain. Evidence for the existence of this system in the non-muscle mucosal cells of the gastrointestinal tract, which is the barrier to drug absorption, has not been found. The system is located on the inner membrane of the mitochondria, an intracellular organelle and its functions are to transport fatty acids across the mitochondria membrane and lead to intraorganelle concentration and oxidation of the fatty acids. There is no evidence to indicate that acylcarnitines will promote transmembrane movement of another target molecule. Carnitine can transverse membranes, however, carnitine alone has no effect in the instant application. The acylcarnitine ester is required for the absorption promoting effect. Thus, the intramitochondrial transport of fatty acids, which is a known function of carnitine, is unrelated to its function as a gastrointestinal drug absorption promoter.

The use of acylcarnitines to promote gastrointestinal absorption affords several advantages over the prior art's non-related absorption promoting compounds. The acylcarnitines, especially these with medium chain fatty acid components, are more potent than the presently used absorption promoting agents. As an example, in aqueous solutions, the acylcarnitines are effective absorption promoting agents at levels as low as 0.05%. By contrast, the effective dose of other known absorption promoters is significantly higher: sodium salicylate—1%, surfactants—1%, chelating agents—2%. This difference in potency affords opportunities for reducing the required size of the dosage form and potentially minimizing side effects. The acylcarnitines cause reversible changes in gastrointestinal permeability to the target drug, indicating that a permanent change has not occurred. Other promoting agents, such as the surfactants, cause a relatively permanent change in gastrointestinal permeability, which is only overcome by turnover of the mucosal cells, a process which may require days for completion. By contrast, removal of acylcarnitines from the gastrointestinal tract results in reversion to normal permability properties in less than 2 hours. This provides a significant advantage in that a rapid and reversible increase in drug absorption does not allow prolonged intervals during which potentially toxic or otherwise harmful agents might also be absorbed. Another potential advantage of the acylcarnitines is that, unlike chelating agent such as EDTA, the acylcarnitines may not necessarily sequester divalent cations ($Mg^{++}$ or $CA^{++}$) which are necessary for the normal functioning of cells. In other words, there is no tissue damage at concentrations of acylcarnitines which significantly increase drug absorption. In contrast to this, studies have indicated that surfactant activity, as with sodium lauryl sulfate, is generally associated with some degree of cellular damage. This lack of tissue damage affords a significant advantage to the use of acylcarnitines in promoting gastrointestinal drug absorption which can be metabolized through normal pathways in the body. This eliminates a potential problem from introducing substances which are not normally present in the biochemical pathways of the body (e.g. salicylates, EDTA etc.)

SUMMARY OF THE INVENTION

It has been found that when poorly absorbed drugs are administered orally or rectally, the bioavailability of said drugs is increased by administering together with an acylcarnitine absorption enhancing agent.

Accordingly, it is an object of this invention to enhance the bioavailability of poorly absorbed drugs administered orally or rectally by administering therewith an acylcarnitine absorption enhancing agent.

It is an object of the invention to provide a new dosage form utilizing a novel class of acylcarnitines which when administered orally or rectally will provide an increased blood level of the therapeutic agent.

Another object of the invention is to provide an acylcarnitine absorption promoter of gastrointestinal drug absorption at concentrations which do not alter the normal morphology of the mucosal cells.

Still another object of the invention is to provide an acylcarnitine series of absorption agents that are endogenous and can be metabolized through normal pathways available in the body.

Other objects, features and advantages of the invention will be apparent to those skilled in the art from the detailed description of the invention which follows.

All of the foregoing objects are readily attained by providing a method and drug form wherein oral and rectal absorption of poorly absorbed drugs is enhanced. The method comprises the steps of preparing a dosage form suitable for oral or rectal delivery, and a dosage form comprising an effective unit dosage amount of the poorly absorbed drug, an acylcarnitine absorption agent or pharmaceutically acceptable salt thereof, the agent being present in said dosage form in an amount sufficient to be effective in enhancing the rate of the oral and rectal absorption of the therapeutic agent, and pharmaceutically acceptable excipients.

DETAILED DESCRIPTION OF THE INVENTION

The present invention, generally comprises the steps of preparing a dosage form capable of being orally or rectally administered, wherein the dosage form comprises an effective unit dosage amount of a poorly absorbed drug and an acylcarnitine absorption enhancing agent, the acylcarnitine agent being present in the dosage form in a sufficient quantity to be effective in enhancing oral and rectal absorption rates and administering the dosage form to warm-blooded animals. The amount of poorly absorbed drug varies over a wide range, but generally the therapeutically effective unit dosage amount of the selected poorly absorbed drug depends on that amount known in the art to obtain the desired results.

The compounds that are used as absorption enhancers in our method and drug forms are acylcarnitines which are β-acyloxy derivatives of γ-trimethylaminobutyric acid and pharmaceutically acceptable salts thereof of the formula:

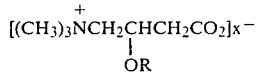

wherein R is:

(a) $C_2$–$C_{20}$ saturated acyl such as acetyl, hexanoyl, octanoyl, lauroyl, myristoyl, palmitoyl, stearoyl and the like;

(b) $C_2$–$C_{20}$ acyl with 1 to 6 double bonds such as 2-hexenoyl, 9-decenoyl, 9-hexadecenoyl (palmitoleoyl), oleoyl, myristoleoyl, 9,12-hexadecadienoyl, α-linoleoyl, γ-linolenoyl, arachidyl and the like;

(c) $C_2$–$C_{20}$ hydroxyacyl with 1 to 3 hydroxy groups such as 2-hydroxylauroyl, 2-hydroxymyristoyl, 2-hydroxypalmitoyl and the like;

(d) $C_4$–$C_{20}$ ketoacyl such as 6-ketodecanoyl, 4-keto-9,11,13-octadecatrienoyl and the like;

(e) $C_5$–$C_{20}$ unsaturated hydroxyacyl such as 2-hydroxy-12-octadecenoyl and the like;

(f) $C_5$–$C_{20}$ carbalkoxyacyl such as ω-ethoxycarbonyloctanoyl and the like; and X is a pharmaceutically acceptable counterion such as chloride, sulfate, nitrate, perchlorate, bromide, phosphate, acetate, benzoate, tartrate, citrate, propionate, gluconate, lactate, maleate, fumarate, bezylate, camsylate, esylate, gluceptate, mesylate, napsylate and the like.

The preferred oral and rectal absorption enhancing agents of the above formula are:

1. Acetylcarnitine
2. Hexanoylcarnitine
3. Lauroylcarnitine
4. Octanoylcarnitine
5. Myristoylcarnitine
6. Palmitoylcarnitine
7. Stearoylcarnitine
8. 2-Hexenoylcarnitine
9. 9-Decenoylcarnitine
10. 9-Hexadecenoylcarnitine
11. α-Linoleoylcarnitine
12. 2-Hydroxylauroylcarnitine
13. 2-Hydroxymyristoylcarnitine
14. 6-Keto-decanoylcarnitine
15. 12-Hydroxy-12-octadecenoylcarnitine
16. ω-Ethoxylcarbonyloctanoylcarnitine
17. 2-Hydroxypalmitolylcarnitine.

The most preferred absorption enhancing agents useful in our method and dosage forms are:

1. Acetylcarnitine
2. Hexanoylcarnitine
3. Octanoylcarnitine
4. Lauroylcarnitine
5. Myristoylcarnitine
6. Palmitoylcarnitine
7. Stearoylcarnitine.

The acylcarnitine absorption enhancing agents employed in the practice of this invention are known compounds which are commercially available and processes for their preparation are disclosed throughout the art.

Various active agents provide beneficial effects when administered to patients. Such agents which can be made more useful by enhancing its absorption in accordance with this invention, are exemplified by, but not limited to, the following classes of drugs:

(1) β-lactam antibiotics such as cefoxitin, N-formamidinylthienamycin, amoxicillin, ampicillin, azlocillin, bacampicillin, carbenicillin, cefaclor, cefadroxil, cefamandole, cefaparole, cefatrizine, cefazoline, cefonicid, cefaperazone, ceforanide, cefotaxime, cefotiam, cefroxadine, cefsulodin, ceftazidime, ceftizoxime, cephalaxin, cephaloglycin, cephaloridine, cephradine, cyclacillin, cloxacillin, dicloxacillin, floxacillin, hetacillin, methicillin, nafcillin, oxacillin, sarmoxacillin, sarpicillin, talampicillin, ticaricillin, penicillin G, penicillin V, pivampicillin, piperacillin, pirbenicillin and the like.

(2) Aminoglycoside antibiotics such as gentamycin, amikacin, astromicin, betamicin, butikacin, butirosin, clindamycin, josamycin, kanamycin, neomycin, netilmicin, tobramycin and the like.

(3) Antiviral agents such as ara C (cytarabine), acyclovir, floxuridine, ribavirin, vidarabine, idoxuridine, trifluridine and the like.

(4) Amino acids such as methyldopa, carbidopa, levodopa, fludalamine, α-aminobutyric acid and the like.

(5) Smooth muscle relaxants such as theophylline, aminophylline, diphylline, oxtriphylline, ambuphylline, fenethylline, guathylline, pentoxyfylline, xanthinol niacinate, theophylline glycinate, glucophylline and the like.

(6) Polypeptides such as cyclo(N-Ala-Tyr-D-Trp-Lys-Val-Phe)acetate (363,586), somatostatin, insulin, gastrin, caerulein, cholecystokinin and the like.

(7) Anti-inflammatory agents such as indomethacin, sulindac, ibuprofen and the like.

(8) Diuretics such as aldactone, hydrochlorothiazide, amiloride, amiloride and hydrochloride and the like.

The enhancement of drug absorption in accordance with this invention is not by any means limited to the above drugs, but are in general applicable to other classes of drugs such as analgesics, anabolics, androgens, anorexics, adrenergics, antiadrenergics, antiallergics, antibacterials, anticholinergics, antidepressants, antidiabetics, antifungal agents, antihypertensives, antineoplastics, antipsychotics, sedatives, cardiovascular agents, antiulcer agents, anticoagulants, anthelmintics, radio-opaques, radio-nuclide diagnostic agents and the like.

Generally, the amount of adjuvant employed in the practice of the invention ranges from 0.05–500 mg in each unit dose. The percentage of adjuvant in the total combination of drug plus adjuvant is 0.05–50% with a preferred ratio of adjuvant in the total combination of adjuvant plus drug being 0.05–25%.

For oral administration, the formulations may be prepared as liquids, suspensions, capsules, tablets, coated tablets, and other standard procedures known in the art. The preferred formulation is a compressed tablet composed of a minimum of 1 mg acylcarnitine ester with the pharmacologically required dose of drug and sufficient excipients to formulate an acceptable composition. For rectal application, the formulations may be prepared as microenemas, suppositories, rectal tablets, and other standard procedures known in the art. The preferred formulation is a solid suppository composed of a minimum of 1 mg acylcarnitine ester with the pharmacologically required dose of drug and sufficient suppository base to formulate an acceptable composition. The methods and choice of excipients and suppository bases are well known to those skilled in the art and the composition of said formulations is not limited to compressed tablets or solid suppositories by this invention.

The following examples illustrate preparation of various compositions of the invention. The examples should be construed as illustrations rather than limitations thereof.

EXAMPLE 1

Effect of palmitoylcarnitine chloride on the rectal absorption of drug entities. Experiments were performed with rats wherein each animal received an aqueous microenema applied to the rectal cavity. The microenemas contained target drug entity (amount shown in table) in the presence or absence of 5 mg palmitoylcarnitine. Blood levels were monitored and the amount of drug absorbed calculated against intravenous administration and expressed as percent bioavailability.

| | | | Percent Bioavailability (mean ± SD) | |
|---|---|---|---|---|
| Target Drug | Dose | Drug Class | Control | with Palmitoylcarnitine-Cl |
| Sodium cefoxitin | 2.5 mg | β-lactam antibiotic | 2 ± 1.1 | 68 ± 7.2 |
| Gentamicin sulfate | 2.5 mg | aminoglycoside antibiotic | 4 ± 1.2 | 42 ± 5.2 |
| Cytarabine | 2.5 mg | anti-viral anti-neoplastic | 0.5 ± 0.1 | 9 ± 0.6 |
| Theophylline | 2.5 mg | smooth muscle relaxant | 75 ± 3.3 | 75 ± 2.6 |
| **#-363,586 | 0.1 mg | polypeptide | 7 ± 3.5 | 100 ± 28.2 |
| Methyldopa | 2.5 mg | cardiovascular anti-hypertensive | 6 ± 0.3 | 100 ± 8.9 |

**cyclo(N—Me—Ala—Tyr—D-Trp—Lys—Val—Phe)acetate

EXAMPLE 2

Concentration dependence of palmitoylcarnitine effect on rectal absorption of sodium cefoxitin, a β-lactam antibiotic. Each animal received an aqueous microenema at pH 6 containing 2.5 mg sodium cefoxitin in the presence or absence of varying amounts of palmitoylcarnitine. Blood samples were collected and assayed for sodium cefoxitin. The amount of drug absorbed is expressed as percent bioavailability as compared to intravenous administration.

| Dose of Palmitoylcarnitine-Cl (mg) | Sodium Cefoxitin Percent Bioavailability mean ± SD |
|---|---|
| 0 | 2 ± 1.1 |
| 0.025 | 1 ± 0.4 |
| 0.125 | 22 ± 3.6 |
| 0.25 | 43 ± 8.0 |
| 1.25 | 81 ± 13.1 |
| 2.5 | 67 ± 9.0 |
| 5.0 | 68 ± 7.2 |

EXAMPLE 3

Effect of various carnitine esters on rectal absorption of sodium cefoxitin, a β-lactam antibiotic, and cyclo(N-Ala-Tyr-D-Trp-Lys-Val-Phe)acetate, a polypeptide. Each animal received an aqueous microenema, pH 6, containing 2.5 mg sodium cefoxitin or 0.1 mg cyclo(N-Ala-Tyr-D-Trp-Lys-Val-Phe)acetate and 5.0 mg various carnitine esters of the general formula of this invention. Blood samples were collected and sodium cefoxitin or cyclo(N-AlA-TyR-D-Trp-Lys-Val-Phe)acetate assayed. The amount of drug absorbed is expressed as percent bioavailability versus intravenous administration.

| | Percent Bioavailability (mean ± SD) | |
|---|---|---|
| Carnitine Ester | Sodium Cefoxitin* | ** |
| None | 2 ± 1.1 | 7 ± 3.5 |
| Acetylcarnitine-Cl | 6 ± 3.4 | 39 ± 21.9 |
| Hexanoylcarnitine-Cl | 2 ± 1.3 | 33 ± 5.6 |
| Octanoylcarnitine-Cl | 7 ± 2.8 | 3 ± 1.1 |
| Lauroylcarnitine-Cl | 51 ± 8.7 | 23 ± 2.5 |
| Myristoylcarnitine-Cl | 27 ± 2.1 | 100 ± 45.0 |
| Palmitoylcarnitine-Cl | 68 ± 7.2 | 100 ± 28.2 |
| Stearoylcarnitine-Cl | 52 ± 2.7 | 26 ± 5.1 |

*β-lactam antibiotic
**Cyclo(N—Ala—Tyr—D-Trp—Lys—Val—Phe)acetate

EXAMPLE 4

Importance of carnitine-palmitoyl ester linkage in absorption promoting effects on rectal sodium cefoxitin absorption. Each animal received an aqueous microenema, pH 6, containing 2.5 mg sodium cefoxitin in the presence or absence of 5.0 mg palmitic acid, carnitine or palmitoylcarnitine. Blood was collected and sodium cefoxitin measured. Absorption of sodium cefoxitin is expressed as percent bioavailability versus intravenous administration.

| Compound | Sodium Cefoxitin Percent Bioavailability (mean ± SD) |
|---|---|
| None | 2 ± 1.1 |
| Palmitic acid | 1 ± 0.8 |
| Carnitine | 1 ± 0.6 |
| Palmitoylcarnitine-Cl | 68 ± 7.2 |

EXAMPLE 5

Reversibility of absorption promoting effect of carnitine esters/histological evaluation of mucosal surface. Two separate experiments demonstrate that carnitine esters cause no permanent change in rectal mucosal tissue at concentrations which effectively increase drug absorption. In experiment A, animals are treated with 5.0 mg palmitoylcarnitine alone and then tested for sodium cefoxitin absorption either immediately or after 1 hour or 2 hours of recovery. Sodium cefoxitin absorption is expressed as percent bioavailability and indicates the reversibility of the absorption promoting effect upon removal of the carnitine ester. In experiment B, animals are exposed to varying concentrations of palmitoylcarnitine for 20 minutes, and the tissue examined histologically for changes in responses to treatment.

| A | | B | |
|---|---|---|---|
| Interval Between Administrations (min) | Sodium Cefoxitin Percent Bioavailability (mean ± SD) | Palmitoylcarnitine Dose (mg) | Histological Evaluation |
| 0 | 68 ± 7.2 | 5.0 | Negligible morphological changes |
| 60 | 36 ± 9.2 | 2.5 | normal |
| 120 | 9 ± 6.6 | 1.25 | normal |
| | | 0.25 | normal |
| | | 0.125 | normal |

-continued

| A | | B | |
|---|---|---|---|
| Interval Between Administrations (min) | Sodium Cefoxitin Percent Bioavailability (mean ± SD) | Palmitoylcarnitine Dose (mg) | Histological Evaluation |
| | | 0.025 | normal |

EXAMPLE 6

Effect of palmitoylcarnitine chloride on small intestinal absorption of polypeptides. Experiments were performed with rats wherein each animal received an aqueous solution applied to the duodenal region. The solutions contained target drug entity 0.1 mg, [cyclo(N-Ala-Tyr-D-Trp-Lys-Val-Phe)acetate] in the presence or absence of 5 mg palmitoylcarnitine. Blood levels were monitored and the amount of polypeptide absorbed calculated against intravenous administration and expressed as percent bioavailability.

| Adjuvant | Percent Bioavailability (mean ± SD) |
|---|---|
| None | 1 |
| Palmitoylcarnitine-Cl | 11 ± 2.7 |

What is claimed is:

1. A method of enhancing the rate of gastrointestinal absorption of an orally or rectally administered poorly absorbed drug selected from the group consisting of β-lactam antibiotics, aminoglycoside antibiotics, antiviral agents, amino acids, smooth muscle relaxants and polypeptides, said method comprising the steps of preparing a dosage form capable of being orally or rectally absorbed, said dosage form comprising a therapeutically effective dosage amount of said drug and an absorption enhancing effective amount of an acylcarnitine agent of the formula:

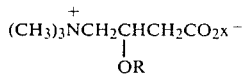

wherein R is saturated acyl($C_2$–$C_{20}$), acyl($C_2$–$C_{20}$) with 1 to 6 double bonds, hydroxyacyl($C_2$–$C_{20}$) with 1 to 3 hydroxy groups, ketoacyl($C_4$–$C_{20}$), unsaturated hydroxyacyl($C_5$–$C_{20}$) or carbalkoxyacyl($C_5$–$C_{20}$) and X is a pharmaceutically acceptable counterion.

2. The method of claim 1 wherein the agent is selected from the group consisting of acetylcarnitine, hexanoylcarnitine, octanoylcarnitine, lauroylcarnitine, myristoylcarnitine, palmitoylcarnitine and stearoylcarnitine.

3. A pharmaceutical composition for enhancing gastrointestinal tract absorption of an orally or rectally administered formulation comprising a therapeutically effective dosage amount of a poorly absorbed drug selected from the group β-lactam antibiotics, aminoglycoside antibiotics, antiviral agents, amino acids, smooth muscle relaxants and polypeptides and an absorption enhancing effective amount of an acylcarnitine agent of the formula:

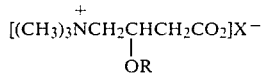

wherein R is saturated acyl($C_2$–$C_{20}$), acyl($C_2$–$C_{20}$) with 1 to 6 double bonds, hydroxyacyl($C_2$–$C_{20}$) with 1 to 3 hydroxy groups, ketoacyl($C_4$–$C_{20}$), unsaturated hydroxyacyl($C_5$–$C_{20}$) or carbalkoxyacyl($C_5$–$C_{20}$) and X is a pharmaceutically acceptable counterion.

4. The composition of claim 3 wherein the acylcarnitine agent is selected from the group consisting of acetylcarnitine, hexanoylcarnitine, lauroylcarnitine, octanoylcarnitine, myristoyl-carnitine, palmitoylcarnitine, stearoylcarnitine, 2-hexenoyl-carnitine, 9-decenoylcarnitine, 9-hexadecenoylcarnitine, α-linoleoylcarnitine, 2-hydroxylauroylcarnitine, 2-hydroxymyristoyl-carnitine, 6-keto-decanoyl-carnitine, 12-hydroxy-12-octadecenoylcarnitine, ω-ethoxycarbonyloctanoylcarnitine and 2-hydroxypalmitoylcarnitine.

5. The composition of claim 4 wherein the drug is an Antibiotic selected from the group consisting of cefoxitin, ampicillin, cefamanodole, cefazoline, cefotaxime, cefaclor, cefalothin, cefitizoxime, amoxicillin, N-formamidinylthienamycin, cefadroxil, gentamycin, neomycin, clindamycin, astromicin and betamicin and the agent is selected from the group consisting of acetylcarnitine, hexanoylcarnitine, octanoylcarnitine, lauroylcarnitine, myristoylcarnitine, palmitoylcarnitine and stearoylcarnitine.

6. The composition of claim 5 wherein the drug is cefoxitin and the agent is palmitoylcarnitine.

7. The composition of claim 5 wherein the drug is gentamicin and the agent is palmitoylcarnitine.

8. The composition of claim 4 wherein the drug is an Antiviral agent selected from the group consisting of cytarabine, acylclovir, trifluridine and vidarabine and the agent is selected from the group consisting of acetylcarnitine, hexanoylcarnitine, octanoylcarnitine, lauroylcarnitine, myristoylcarnitine, palmitoylcarnitine and stearoylcarnitine.

9. The composition of claim 8 wherein the drug is cytarabine and the agent is palmitoylcarnitine.

10. The composition of claim 4 wherein the drug is an Amino acid selected from the group consisting of methyldopa, carbidopa, α-aminobutyric acid and levadopa and the agent is selected from the group consisting of acetylcarnitine, hexanoylcarnitine, octanoylcarnitine, lauroylcarnitine, myristoylcarnitine, palmitoylcarnitine and stearoylcarnitine.

11. The composition of claim 10 wherein the Amino acid is methyldopa and the agent is palmitoylcarnitine.

12. The composition of claim 4 wherein the drug is a smooth Muscle relaxant selected from the group consisting of theophylline, aminophylline, xanthinol niacinate, glucophylline and the agent is selected from the group consisting of acetylcarnitine, hexanoylcarnitine, octanoylcarnitine, lauroylcarnitine, myristoylcarnitine, palmitoylcarnitine and stearoylcarnitine.

13. The composition of claim 12 wherein the smooth Muscle relaxant is theophylline and the agent is palmitoylcarnitine.

14. The composition of claim 4 wherein the drug is a Polypeptide selected from the group consisting of gastrin, somatostatin, insulin and cyclo(N-Me-Ala-Tyr-D-Trp-Lys-Val-Phe)acetate and the agent is selected from the group consisting of acetylcarnitine, hexanoylcarnitine, octanoylcarnitine, lauroylcarnitine, myristoylcarnitine, palmitoylcarnitine and stearoylcarnitine.

15. The composition of claim 14 wherein the Polypeptide is cyclo(N-Ala-Tyr-D-Trp-Lys-Val-Phe)acetate and the agent is palmitoylcarnitine.

16. The composition of claim 3 further comprising pharmaceutically acceptable excipients.

* * * * *